United States Patent
Hallinan et al.

(10) Patent No.: US 9,428,434 B2
(45) Date of Patent: Aug. 30, 2016

(54) WATER CONTROL IN ACETIC ACID PRODUCTION PROCESSES

(71) Applicant: LyondellBasell Acetyls, LLC, Houston, TX (US)

(72) Inventors: Noel C. Hallinan, Loveland, OH (US); John D. Hearn, Beach City, TX (US); David L. Ramage, Friendswood, TX (US); Brian A. Salisbury, Beach City, TX (US); Daniel F. White, Houston, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 0 days.

(21) Appl. No.: 14/964,793

(22) Filed: Dec. 10, 2015

(65) Prior Publication Data

US 2016/0168066 A1 Jun. 16, 2016

Related U.S. Application Data

(60) Provisional application No. 62/090,914, filed on Dec. 12, 2014.

(51) Int. Cl.
*C07C 51/12* (2006.01)

(52) U.S. Cl.
CPC .................................... *C07C 51/12* (2013.01)

(58) Field of Classification Search
CPC ...................................................... C07C 51/12
USPC ........................................................ 562/519
See application file for complete search history.

(56) References Cited

U.S. PATENT DOCUMENTS

| 4,909,939 | A | * | 3/1990 | Rickelton | C02F 1/26 210/634 |
| 5,817,869 | A | * | 10/1998 | Hinnenkamp | C07C 51/12 562/519 |
| 5,932,764 | A | * | 8/1999 | Morris | C07C 51/12 562/519 |
| 6,362,366 | B1 | | 3/2002 | Hallinan et al. | |
| 6,552,221 | B1 | * | 4/2003 | Hallinan | B01J 19/0006 562/519 |

OTHER PUBLICATIONS

PCT/US2015/065039 International Search Report and Written Opinion mailed Apr. 18, 2016.

* cited by examiner

*Primary Examiner* — Sikarl Witherspoon

(57) ABSTRACT

Processes for producing acetic acid are presented herein. One or more embodiments include processes for controlling downstream water concentration in acetic acid production process including contacting methanol and carbon monoxide in the presence of a reaction medium under carbonylation conditions sufficient to form a carbonylation product including acetic acid, wherein the reaction medium includes a carbonylation catalyst, water in an upstream water concentration of from 1 wt. % to 14 wt. % water, and a tertiary phosphine oxide; recovering acetic acid from the carbonylation product; and controlling a downstream water concentration by determining a target water concentration and introducing the tertiary phosphine oxide to the reaction medium at a rate, basicity, concentration or combination thereof sufficient to provide a downstream water concentration within 1 wt. % of the target water concentration.

20 Claims, 3 Drawing Sheets

WATER CONTROL IN ACETIC ACID PRODUCTION PROCESSES

CROSS-REFERENCE TO RELATED APPLICATIONS

This application claims benefit of priority to U.S. Provisional Application No. 62/090,914 filed on Dec. 12, 2014, which is incorporated herein by reference in its entirety.

STATEMENT REGARDING FEDERALLY SPONSORED RESEARCH OR DEVELOPMENT

Not applicable.

BACKGROUND

1. Field

The present disclosure generally relates to acetic acid production processes. In particular, embodiments contained herein relate to water control in acetic acid production processes.

2. Related Art

This section introduces information from the art that may be related to or provide context for some aspects of the techniques described herein and/or claimed below. This information is background facilitating a better understanding of that which is disclosed herein. This is a discussion of "related" art. That such art is related in no way implies that it is also "prior" art. The related art may or may not be prior art. The discussion is to be read in this light, and not as admissions of prior art.

Acetic acid may be commercially produced by methanol carbonylation. Methanol carbonylation processes often utilize a promoter, such as methyl iodide, in addition to carbonylation catalyst. The addition of additives to the process can suppress hydrogen iodide volatilization in downstream processes, which can allow reaction operation at lower water concentrations. However, the benefits of low water concentrations in the reaction, such as decreased water gas shift and decreased propionic acid etc., can lead to insufficient water in downstream processes.

Contained herein are embodiments directed to resolving, or at east reducing, one or all of the problems mentioned above.

SUMMARY

Embodiments disclosed herein include processes for producing acetic acid. In one or more embodiments, the processes generally include acetic acid production processes. One or more embodiments include processes for controlling downstream water concentration in acetic acid production process including contacting methanol and carbon monoxide in the presence of a reaction medium under carbonylation conditions sufficient to form a carbonylation product including acetic acid, wherein the reaction medium includes a carbonylation catalyst, water in an upstream water concentration of from 1 wt. % to 14 wt. % water, and a tertiary phosphine oxide; recovering acetic acid from the carbonylation product; and controlling a downstream water concentration by determining a target water concentration and introducing the tertiary phosphine oxide to the reaction medium at a rate, basicity, concentration or combination thereof sufficient to provide a downstream water concentration within 1 wt. % of the target water concentration.

One or more embodiments include the process of the preceding paragraph, wherein the recovering acetic acid includes flashing the carbonylation product to form a vapor fraction and a liquid fraction; separating the vapor stream to form an overhead stream, an acetic acid stream and a bottoms stream; and drying the acetic acid stream to remove water therefrom.

One or more embodiments include the process of any preceding paragraph, wherein the downstream water concentration is selected from a concentration of water in the carbonylation product, the vapor fraction, the acetic acid stream or combinations thereof.

One or more embodiments include the process of any preceding paragraph, wherein the upstream water concentration is from 2 wt. % to 6 wt. %.

One or more embodiments include the process of any preceding paragraph, wherein the target water concentration is greater than the upstream water concentration.

One or more embodiments include the process of any preceding paragraph, wherein the target water concentration is from 4 wt. % to 15 wt. %.

One or more embodiments include the process of any preceding paragraph, wherein a differential between the upstream and target water concentration is at least 1 wt. %.

One or more embodiments include the process of any preceding paragraph, wherein a differential between the upstream and target water concentration is less than 10 wt. %.

One or more embodiments include the process of any preceding paragraph, wherein a differential between the upstream and target water concentration is from 2 wt. % to 6 wt. %.

One or more embodiments include the process of any preceding paragraph, wherein the reaction medium includes a tertiary phosphine oxide concentration of from 0.2M to 1.0M.

One or more embodiments include the process of any preceding paragraph, wherein the downstream water concentration is controlled by increasing basicity of the tertiary phosphine oxide with an increasing target water concentration.

One or more embodiments include the process of any preceding paragraph, wherein the downstream water concentration is controlled by increasing a tertiary phosphine oxide concentration with an increasing differential between the upstream and target water concentration.

One or more embodiments include the process of any preceding paragraph, wherein the tertiary phosphine oxide includes a plurality of tertiary phosphine oxides.

One or more embodiments include the process of any preceding paragraph, wherein the tertiary phosphine oxide is selected from non-benzoyl containing pentavalent phosphine oxides, compound mixtures of at least four phosphine oxides and pentavalent aryl or alkaryl phosphine oxides comprising one or more benzoyl groups.

One or more embodiments include the process of any preceding paragraph, wherein the tertiary phosphine oxide is selected from non-benzoyl containing pentavalent phosphine oxides, compound mixtures of at least four phosphine oxides and combinations thereof.

One or more embodiments include the process of any preceding paragraph, wherein the carbonylation conditions include a temperature of from 150° C. to 250° C. and a pressure of from 200 psig (1380 kPa) to 2000 psig (13800 kPa).

One or more embodiments include the process of any preceding paragraph, wherein the recovery of acetic acid is in the absence of supplemental water addition.

One or more embodiments include an acetic acid production process including contacting methanol and carbon monoxide in the presence of a reaction medium under carbonylation conditions sufficient to form a carbonylation product including acetic acid, wherein the reaction medium comprises a carbonylation catalyst, water in an upstream water concentration of from 2 wt. % to 6 wt. % water, and a tertiary phosphine oxide; flashing the carbonylation product to form a vapor fraction and a liquid fraction; separating the vapor stream to form an overhead stream, an acetic acid stream and a bottoms stream; drying the acetic acid stream to remove water therefrom; and controlling a downstream water concentration by introducing the tertiary phosphine oxide to the reaction medium at a rate, basicity, concentration or combination thereof sufficient to provide a downstream water concentration that is greater than the upstream water concentration and is from 4 wt. % to 15 wt. %, wherein the downstream water concentration is selected from a concentration of water in the carbonylation product, the vapor fraction, the acetic acid stream or combinations thereof.

One or more embodiments include the process of the preceding paragraph, wherein a differential between the upstream and target water concentration is from 2 wt. % to 10 wt. %.

One or more embodiments include the process of any preceding paragraph, wherein the tertiary phosphine oxide is selected from non-benzoyl containing pentavalent phosphine oxides, compound mixtures of at least four phosphine oxides and pentavalent aryl or alkaryl phosphine oxides comprising one or more benzoyl groups.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

Figure 1:
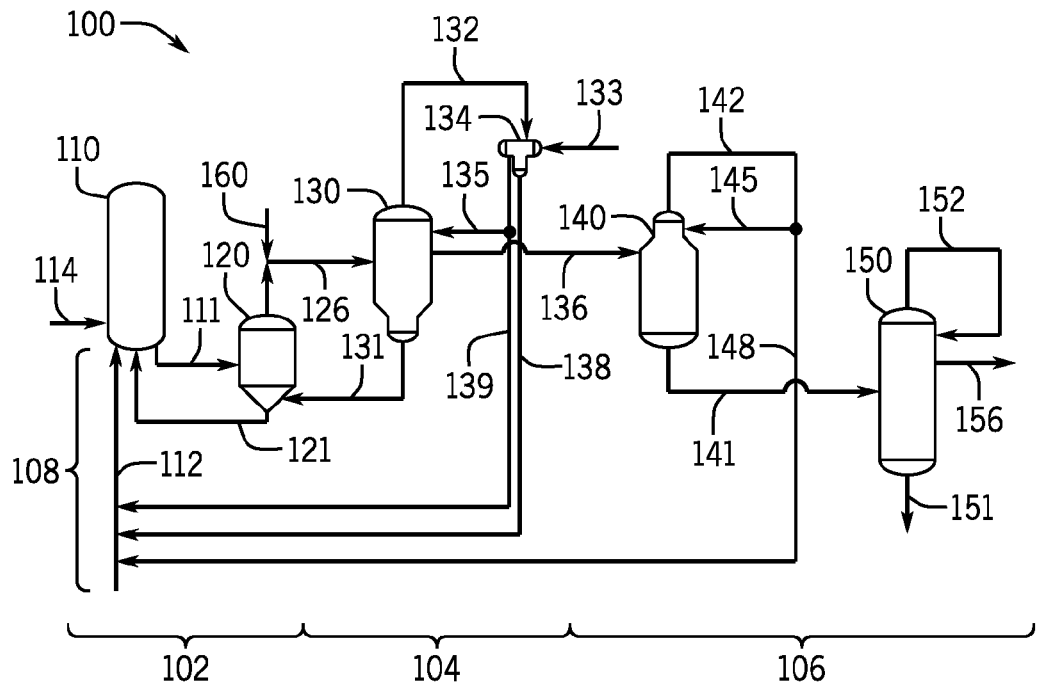
FIG. 1 illustrates a schematic of one or more embodiments of the disclosed process.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

In the description below, unless otherwise specified, all compounds described herein may be substituted or unsubstituted and the listing of compounds includes derivatives thereof. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

Embodiments described herein generally include processes for producing carboxylic acids. It will be realized that while specific embodiments herein may refer to acetic acid (often referred to as HOAc) production processes, it is to be understood by one skilled in the art that such embodiments may be utilized in other carboxylic acid production processes. Furthermore, one or more specific embodiments include production of glacial acetic acid (which is encompassed by the term "acetic acid" as referenced herein). Glacial acetic acid refers to acetic acid that is generally undiluted (includes a water concentration at most in the parts per million range).

The acetic acid production processes generally include carbonylation processes. For example (and for purposes of discussion herein), the acetic acid production processes may include the carbonylation of methanol or its derivatives to produce acetic acid. As referenced previously herein, the embodiments described herein are also applicable to the carbonylation of higher homologues of methanol, such as ethanol, butanol and pentanol, for example, to produce acids which are higher homologues of acetic acid. The adaptation of the embodiments to such systems will be readily apparent to the artisan given the following discussion.

Carbonylation processes generally include reacting an alcohol, such as methanol, with carbon monoxide in a liquid reaction medium under carbonylation conditions sufficient to form acetic acid and recovering the formed acetic acid from the process.

The reaction medium generally includes a carbonylation catalyst. Suitable carbonylation catalysts include those known in the art, such as rhodium catalysts, iridium catalysts and palladium catalysts. Suitable rhodium catalysts include rhodium metal and rhodium compounds selected from rhodium salts, rhodium oxides, rhodium acetates, organo-rhodium compounds, coordination compounds of rhodium and mixtures thereof, for example. (See, U.S. Pat. No. 5,817,869, which is incorporated in its entirety herein.) Suitable iridium catalysts include iridium metal and iridium compounds selected from acetates, oxalates, acetoacetates and mixtures thereof, for example. (See, U.S. Pat. No. 5,932,764, which is incorporated in its entirety herein.)

The concentration of carbonylation catalyst utilized in the reaction medium may be from 1 mmol to 100 mmol, or from 2 mmol to 5 mmol, or at least 7.5 mmol, or from 2 mmol to 75 mmol, or from 5 mmol to 50 mmol, or from 7.5 mmol to 25 mmol of catalyst per liter of reaction medium, for example.

In one or more embodiments, the carbonylation catalyst is utilized with a co-catalyst. The co-catalyst may include those known in the art. For example, the co-catalyst may be selected from metal and metal compounds selected from osmium, rhenium, ruthenium, cadmium, mercury, zinc, gallium, indium, tungsten and mixtures thereof.

In one or more embodiments, the reaction medium includes from 2 wt. % to 14 wt. %, or 10 wt. % or less, or 8 wt. % or less, or 6 wt. % or less, or from 1 wt. % to 5 wt. %, or from 4 wt. % to 8 wt. % water based on the total weight of the reaction medium, for example. In one or more embodiments, the concentration of water in the reaction medium is referred to as an upstream water concentration.

The reaction medium may further include a variety of additives or other components (i.e., components other than the alcohol, carbon monoxide and carbonylation catalyst). The introduction of such additives to the reaction medium can be via any method known in the art. For example, each of the additives may be, either independently or as a mixture, introduced directly to the reaction medium. Alternatively, one or more of the additives may be generated in-situ, for example.

In the embodiments described herein, the additives include a tertiary phosphine oxide. The tertiary phosphine oxide is generally represented by the formula $R_3PO$, where R is alkyl or aryl, O is oxygen, P is phosphorous.

In one or more embodiments, the tertiary phosphine oxide includes a compound mixture of at least four phosphine oxides, where each phosphine oxide has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof. Each phosphine oxide has at least 15, or at least 18 total carbon atoms.

Examples of suitable phosphine oxides for use in the compound mixture include, but are not limited to, tri-n-hexylphosphine oxide (THPO), tri-n-octylphosphine oxide (TOPO), tris(2,4,4-trimethylpentyl)-phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo[3.3.1]nonane-9-oxide, dihexylmonooctylphosphine oxide, dioctylmonohexylphosphine oxide, dihexylmonodecylphosphine oxide, didecylmonohexylphosphine oxide, dioctylmonodecylphosphine oxide, didecylmonooctylphosphine oxide, and dihexylmonobutylphosphine oxide and the like.

The compound mixture includes from 1 wt. % to 60 wt. %, or from 35 wt. % to 50 wt. % of each phosphine oxide based on the total weight of compound mixture. In one or more specific, non-limiting embodiments, the compound mixture includes TOPO, THPO, dihexylmonooctylphosphine oxide and dioctylmonohexylphosphine oxide. For example, the compound mixture may include from 40 wt. % to 44 wt. % dioctylmonohexylphosphine oxide, from 28 wt. % to 32 wt. % dihexylmonooctylphosphine oxide, from 8 wt. % to 16 wt. % THPO and from 12 wt. % to 16 wt. % TOPO, for example.

In one or more embodiments, the compound mixture exhibits a melting point of less than 20° C., or less than 10° C., or less than 0° C., for example.

In one or more specific embodiments, the compound mixture is Cyanex®923, commercially available from Cytec Corporation.

Each individual component of the compound mixture is solid while the mixture is liquid at room temperature. As used herein, "room temperature" means that a temperature difference of a few degrees does not matter to the phenomenon under investigation, such as a preparation method. In some environments, room temperature may include a temperature of from about 20° C. to about 28° C. (68° F. to 82° F.), while in other environments, room temperature may include a temperature of from about 50° F. to about 90° F., for example. However, room temperature measurements generally do not include close monitoring of the temperature of the process and therefore such a recitation does not intend to bind the embodiments described herein to any predetermined temperature range.

Mixtures and methods of forming such compound mixtures are described in U.S. Pat. No. 4,909,939, which is incorporated in its entirety herein.

In one or more embodiments, the tertiary phosphine oxide includes a pentavalent aryl or alkaryl phosphine oxide containing one or more benzoyl groups (i.e., benzoyl containing phosphine oxide). These benzoyl groups may be substituted or unsubstituted, for example. In one or more embodiments, the benzoyl containing phosphine oxide may be selected from bis(2,4,6-trimethylbenzoyl) phenyl phosphine oxide (BAPO), (2,4,6-trimethylbenzoyl) diphenyl phosphine oxide (TMDPO) or combinations thereof, for example. While the one or more additives are introduced to the reaction medium, it should be noted that the additives may react with components within the reaction medium. Accordingly, the reaction medium may include the components introduced thereto (e.g., the benzoyl group containing phosphine oxide), any in-situ generated related components due to reaction, such as hydrolysis, and combinations thereof.

In one or more embodiments described herein, the tertiary phosphine oxide includes a pentavalent phosphine oxide (for ease of reference herein and to distinguish from prior referenced benzoyl containing pentavalent phosphine oxides, these compounds will be referred to herein as non-benzoyl group containing pentavalent phosphine oxides). The non-benzoyl containing pentavalent phosphine oxides generally have the formula $R_3P=O$, wherein each R is independently selected from substituted or unsubstituted alkyls, aryls, aralkyls and combinations thereof. For example, each R may be independently selected from methyl, ethyl, propyl, isopropyl, butyl, isobutyl, t-butyl, amyl, pentyl, hexyl, octyl, phenyl, naphthyl and combinations thereof, for example. When substituted, each substituent on each R group may be independently selected from those defined herein above for R, as well as halogens, hydroxyl groups, nitrogen groups, amino groups and combinations thereof, for example. Specific, non-limiting embodiments include triethyl phosphine oxide, tributyl phosphine oxide, tripentyl phosphine oxide, diphenylmethyl phosphine oxide, triphenyl phosphine oxide and combinations thereof, for example. In one or more specific embodiments, the non-benzoyl containing pentavalent phosphine oxides include a phenyl group directly bonded to the phosphorous atom. In one or more specific embodiments, the non-benzoyl containing pentavalent phosphine oxides are selected from tri-butyl phosphine oxide (TBPO), tri-phenyl phosphine oxide (TPPO) and combinations thereof.

In one or more embodiments, the tertiary phosphine oxide includes a plurality of tertiary phosphine oxides. For example, the tertiary phosphine oxide may include a first phosphine oxide and a second phosphine oxide. The plurality of additives may be introduced into the reaction medium in the form of a mixture (with or without additional additives therein) or they may be introduced to the reaction medium separately. However, it is contemplated within the embodiments described herein that at least a portion of the first phosphine oxide and at least a portion of the second phosphine oxide contact the reaction medium nearly simultaneously, e.g., up to about 2 weeks between the separate additions.

In one or more embodiments, the plurality of tertiary phosphine oxides includes greater than 50 mol. %, or at least 60 mol. %, or at least 70 mol. %, or at least 80 mol. %, or at least 90 mol. %, or at least 95 mol. %, or at least 97 mol. %, or at least 98 mol. %, or at least 99 mol. % first phosphine oxide, for example. In one or more embodiments, the plurality of additives includes greater than 50 mol. %, or at least 60 mol. %, or at least 70 mol. %, or at least 80 mol. %, or at least 90 mol. %, or at least 95 mol. %, or at least 97 mol. %, or at least 98 mol. %, or at least 99 mol. % second phosphine oxide, for example. In one or more embodiments, the plurality of additive include at least 10 mol. %, or at least 20 mol. % or from 10 mol. % to 50 mol. % phosphine oxide additive, for example. In alternative embodiments, the plurality of tertiary phosphine oxides is utilized in essentially equal amounts.

The exact concentration of the tertiary phosphine oxide or the total plurality of tertiary phosphine oxides, as well as the concentration of the first tertiary phosphine oxide and the second tertiary phosphine oxide will depend on the specific process conditions, including the particular additives utilized. However, in one or more embodiments, the concentration of the tertiary phosphine oxide (or total concentration of the plurality of phosphine oxides) introduced into the reaction medium may vary from 0.005M to 2.0M, or from 0.02M to 1.0M, or from 0.3M to 0.5M, for example.

The reaction medium may further include an alkyl iodide, such as methyl iodide, for example. The concentration of alkyl iodide in the reaction medium may be from 0.6 wt. % to 36 wt. %, or from 4 wt. % to 24 wt. %, or from 6 wt. % to 20 wt. % based on total weight of reaction medium, for example. Furthermore, the reaction medium may include an alkyl acetate, such as methyl acetate, for example. The concentration of alkyl acetate in the reaction medium may be from 0.6-36, or 2 wt. % to 20 wt. %, or from 2 wt. % to 16 wt. %, or from 3 wt. % to 10 wt. %, or from 2 wt. % to 8 wt. % based on the total weight of the reaction medium, for example. As described previously herein, the introduction of such components to the reaction medium can be via any method known in the art including introduction to the reaction medium or in-situ generation, for example.

It is contemplated that supplemental hydrogen may be supplied to the reaction medium. Supplemental hydrogen may be supplied to the reaction medium to provide a total hydrogen concentration in the reaction medium of from 0.1 mol. % to 5 mol. %, or from 0.3 mol. % to 3 mol. %, for example.

In practice, carbonylation reaction conditions vary depending upon reaction parameters, reactor size and charge and the individual components employed. However, in one or more embodiments, the carbonylation process may be a batch or continuous processes and the carbonylation conditions may include a pressure of from 200 psig (1380 kPa) to 2000 psig (13800 kPa), or from 200 psig (1380 kPa) to 1000 psig (6895 kPa), or from 300 psig (2068 kPa) to 500 psig (3447 kPa), for example and a temperature of from 150° C. to 250° C., or from 170° C. to 220° C., or from 150° C. to 200° C., for example.

Carbonylation processes further include recovering the formed acetic acid from the process. Such recovery can be accomplished by methods known in the art and may include, without limitation, separation and/or purification processes.

In one or more embodiments, the recovery of the formed acetic acid includes withdrawing a reaction mixture (e.g., carbonylation product) from the carbonylation reaction. The reaction mixture may include a variety of components, such as acetic acid, methanol, methyl acetate, methyl iodide, carbon monoxide, carbon dioxide, water, and/or hydrogen iodide, among other components. Accordingly, the recovery may include separating components thereof via a variety of processes known in the art. For example, one or more embodiments may include separating components of the carbonylation product in a flash vessel into a liquid fraction and a vapor fraction. The flash vessel may include any configuration for separating vapor and liquid components via a reduction in pressure. For example, the flash vessel may include a flash tank, nozzle, valve or combinations thereof.

The flash vessel may operate at a pressure below that of the reactor. For example, the flash vessel may operate at a pressure of from 10 psig (70 kPa) to 100 psig (700 kPa), 20 psig (138 kPa) to 90 psig (620 kPa), or from 30 psig (207 kPa) to 70 psig (483 kPa) and a temperature of from 100° C. to 160° C., or from 110° C. to 150° C., or from 120° C. to 140° C. The vapor fraction may include acetic acid and other volatile components, such as methanol, methyl acetate, methyl iodide, carbon monoxide, carbon dioxide, water, hydrogen iodide and combinations thereof. The liquid fraction may include acetic acid, methanol, methyl acetate, methyl iodide, carbon monoxide, carbon dioxide, water, hydrogen iodide and combinations thereof.

In one or more embodiments, the liquid fraction may be recycled to the carbonylation reaction, while the vapor fraction may be passed to a separation unit (which may include one or more individual units including one or more stages) to form an overhead stream, an acetic acid stream and a bottoms stream. The separation unit may include those known in the art, such as one or more distillation columns, for example. In one or more embodiments, the separation unit may operate at an overhead pressure of from 20 psia to 40 psia, or 30 psia to 35 psia and an overhead temperature of from 95° C. to 135° C., or from 110° C. to 135° C. or from 125° C. to 135° C. The separation unit may be operated at a bottom pressure of from 25 psia to 45 psia, or from 30 psia to 40 psia and a bottoms temperature of from 115° C. to 155° C., or from 135° C. to 135° C., for example.

The acetic acid stream may be passed to a drying column to remove water and may be subjected to further separation processes to recover the acetic acid therein.

While low water concentrations can be beneficial in the reaction section, the resultant low water concentrations in the reaction mixture can result in inefficient or incomplete separation of the hydrogen iodide (or halide) from the acetic acid in downstream processes, such as the flash vessel, separation unit and/or drying column. Accordingly, water is often added downstream, such as to the separation column, the liquid fraction, or combinations thereof, to provide for efficient separation.

However, embodiments of the present disclosure provide for the ability to control downstream water concentrations without the need for supplemental water introduction into the downstream sections. The downstream water concentration is controlled by determining a target water concentration and introducing the tertiary phosphine oxide to the reaction medium at a rate, basicity, concentration or combinations thereof, sufficient to achieve the target water concentration. The target water concentration is determined and will vary depending on specific process conditions. However, in one or more embodiments, the target water concentration is greater than the water concentration in the reaction medium (i.e., the upstream water concentration). For example, in one or more embodiments, the target water concentration is from 3 wt. % to 15 wt. %, or from 4 wt. % to 12 wt. %, or from 5 wt. % to 9 wt. %, or at least 6 wt. %. Thus, a differential between the target water concentration and the upstream water concentration may be from 2 wt. % to 10 wt. %, or less than 10 wt. %, of or from 2 wt. % to 6 wt. %, for example. In one or more embodiments, the downstream water concentration is within 0 wt. % to 3 wt. %, or 0.5 wt. % to 2 wt. % or within 1 wt. % of the target water concentration.

The downstream water concentration can be identified as the water concentration at any point within the acetic acid production process subsequent to withdrawal of the reaction mixture from the carbonylation reaction. For example, the downstream water concentration may be the concentration of water in the carbonylation product, the vapor fraction, the acetic acid stream or combinations thereof.

Figure 2:
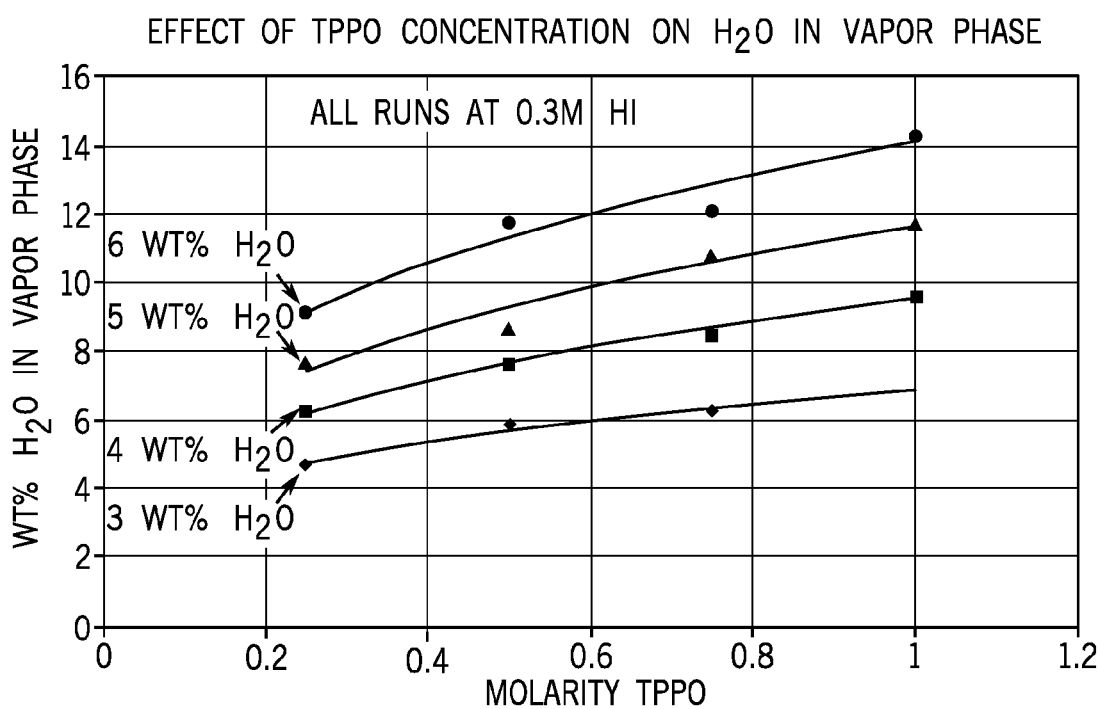
FIG. 2 illustrates Vapor Liquid Equilibria (VLE) data for various process scenarios.

As the target water concentration or the differential between the upstream water concentration and the downstream water concentration increases, the downstream water concentration may be controlled by increasing the tertiary phosphine oxide concentration in the reaction medium. It is recognized the terms "increasing" and "decreasing" are relative terms. However, when utilized with respect to control of downstream water concentration, it is recognized that the terms are referenced as discussed in the Examples herein and are utilized with reference to increasing a value with reference to a real time process variable. For example, control of the downstream water concentration in an acetic acid production process running with an upstream water concentration of 3 wt. % and a TPPO molarity in the reaction medium of 0.5M and a downstream water concentration of 6 wt. % and a target water concentration of 7 wt. % water would include an increase (from the real time TPPO concentration of 0.5M) in the tertiary phosphine oxide concentration to a value closer to 1.0 M (see, FIG. 2 for further illustration).

Alternatively, or in combination with the rate of tertiary phosphine oxide addition or concentration of tertiary phosphine oxide concentration in the reaction medium, the downstream water concentration can be controlled by the basicity of the tertiary phosphine oxide utilized in the reaction medium.

There are many ways to determine the relative basicity of phosphine oxides. For example, those skilled in the art of infrared spectroscopy will understand that the infrared absorption band associated with the P═O (phosphoryl) group in pentavalent compounds is a function of those groups bonded to the phosphorus atom. More strongly basic phosphine oxides are expected to have increased charge separation and decreased double bond character of the P═O group than more weakly basic phosphine oxides. This leads to lower infrared wavenumber values for the P═O bond for more strongly basic oxides. The right hand column of Table 1 below contains the P═O infrared wavenumber values for acetonitrile solutions of 11 phosphine oxides from which it can be observed that, in general, those phosphine oxides containing phenyl or substituted phenyl groups are less basic than those containing alkyl groups. Thus, triphenylphosphine oxide, for example, will be less basic than tributyl phosphine oxide or Cyanex® 923.

TABLE 1

| $R_3PO$ | $^{31}P$ NMR (HOAc) | P═O, FTIR ($CH_3CN$) |
| --- | --- | --- |
| Triphenylphosphate (TOPPO) | −16.8 | 1243 |
| Phenylbis(2,4,6-trimethylbenzoyl) phosphine oxide (POYPO) | 7.3 | 1207 |
| Diphenyl(2,4,6-trimethylbenzoyl) phosphine oxide (DOYPO) | 16.2 | 1207 |
| Trimorpholino phosphine oxide (MORPO) | 19.8 | 1210 |
| Diphenylphosphine oxide (DPPO) | 27.3 | 1184 |
| Triphenylphosphine oxide (TPPO) | 34.5 | 1193 |
| Tris p-tolylphosphine oxide (PTLPO) | 35 | 1184 |
| Cyclohexyldiphenylphosphine oxide (CyDPPO) | 41 | 1187 |
| Ethyldiphenylphosphine oxide (EtDPPO) | 42.1 | 1186 |
| Tricyclohexylphosphine oxide ($Cy_3PO$) | 60 | 1153 |
| Tributylphosphine oxide (TBPO) | 61.4 | 1158 |

Another method for determining a phosphine oxide basicity scale is through $^{31}P$ NMR spectroscopy. Those skilled in this art will realize that increasing basicity of phosphine oxides will directly correlate with deshielding of the phosphorus atom due to charge separation in, and decreased double bond character of the P═O group. As such, chemical shifts in the upfield direction are expected with increasing basicity. $^{31}P$ NMR chemical shifts for acetic acid solutions of the 11 phosphine oxides investigated by infrared spectroscopy are shown in the middle column of Table 1, where the values are relative to that of 85% $H_3PO_4$, which is assigned a value of 0 ppm. Thus, triphenylphosphine oxide, for example, has a much smaller upfield shift of 34.5 ppm relative to TBPO, which has an upfield shift of 61.4. It can be seen that similar directional trends are observed for both infrared and $^{31}P$ NMR spectroscopy. An example of a literature reference in which the same methodology is used is Dalton Transactions 2012, 41, 1742-1754 (http://www-.chem.tamu.edu/rgroup/bluemel/pdf/67%20PDF.pdf).

Accordingly, one or more embodiments include control of downstream water concentration by increasing the basicity of the tertiary phosphine oxide with an increasing target water concentration (such as in the same manner as that described previously herein with reference to tertiary phosphine oxide concentration).

FIG. 1 illustrates a schematic of an embodiment of an acetic acid production process 100. The process 100 is generally described in terms of functional areas, i.e., a reaction area 102, a light-ends area 104, a purification area 106 and a recycle area 108, rather than specific process equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and flash vessel 120. For example, the reaction area 102 may include reactor 110, flash vessel 120, and streams (or portions of streams) 111, 112, 114, 121, 126, 131, 160, 138, 139, 148. The reactor 110 is a reactor or vessel in which methanol is carbonylated in the presence of a catalyst to form acetic acid at elevated pressure and temperature. The flash vessel 120 is a tank or vessel in which a reaction mixture obtained in the reactor, for example the reactor 110, is at least partially depressurized and/or cooled to form a vapor stream and a liquid stream.

The light-ends area 104 may include a separations column, for example, a light-ends column 130, equipment associated with light-ends column 130, and streams associated with the light-ends column 130. For example, the light-ends area 104 may include light-ends column 130, decanter 134, and streams 126, 131, 132, 133, 135, 136, 138, 139, 160. The light-ends column 130 is a fractioning or distillation column and includes any equipment associated with the column, including but not limited to heat exchangers, decanters, pumps, compressors, valves, and the like.

The purification area 106 may include a drying column 140, optionally, a heavy-ends column 150, equipment associated with drying column 140 and heavy-ends column 150, and streams associated with the drying column 140 and heavy-ends column 150. For example, the purification area 106 may include drying column 140, heavy-ends column 150, and streams 136, 141, 142, 145, 148, 151, 152, 156. The heavy-ends column 150 is a fractioning or distillation column and includes any equipment associated with the column, including but not limited to heat exchangers, decanters, pumps, compressors, valves, and the like.

The recycle area 108 may include process streams recycled to the reaction area 102 and/or light-ends area 104. For example, in FIG. 1, the recycle area 108 may include streams 121, 138, 139, 148.

In an embodiment, the reactor 110 may be configured to receive a carbon monoxide feed stream 114 and a methanol or methanol/methyl acetate feed stream 112. A reaction mixture may be withdrawn from the reactor in stream 111. Other streams may be included as known in the art, for example, a stream that may recycle a bottoms mixture of the reactor 110 back into the reactor 110, or a stream may be included to release a gas from the reactor 110. Stream 111 may include at least a part of the reaction mixture.

In an embodiment, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110 (stream 121 may thus be considered in the recycle area 108 and in the reactor area 102). In an embodiment, stream 126 may comprise acetic acid, water, methyl iodide, methyl acetate, HI, and mixtures thereof.

In an embodiment, the light-ends column 130 may include a distillation column and equipment associated with the distillation column including but not limited to a heat exchanger 137, a decanter 134, pumps, compressors, valves, and other related equipment. The light-ends column 130 may be configured to receive stream 126 from the flash vessel 120. Stream 132 includes overhead product from the light-ends column 130, and stream 131 includes bottoms product from the light-ends column 130. Light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor (stream 138 may thus be considered in the recycle area 108, in the light-ends area 104, and in the reactor area 102). Stream 139 may recycle a portion of the light phase of decanter 134 back to the reactor 110 via, for example, stream 112 (stream 139 may thus be considered in the recycle area 108, in the light-ends area 104, and in the reactor area 102). Stream 136 may emit from the light-ends column 130. Other streams may be included as known in the art, for example, a stream that may recycle a bottoms mixture of the light-ends column 130 back into the light-ends column 130. Any stream received by or emitted from the light-ends column 130 may pass through a pump, compressor, heat exchanger, and the like as is common in the art.

In an embodiment, the drying column 140 may comprise a vessel and equipment associated with the vessel including but not limited to heat exchangers, decanters, pumps, compressors, valves, and the like. The drying column 140 may be configured to receive stream 136 from the light-ends column 130. The drying column 140 may separate components of stream 136 into streams 142 and 141.

Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment known in the art, for example, a heat exchanger or separation vessel before streams 145 or 148 recycle components of stream 142. Other streams may be included as known in the art, for example, a stream may recycle a bottoms mixture of the drying column 140 back into the drying column 140. Any stream received by or emitted from the drying column 140 may pass through a pump, compressor, heat exchanger, separation vessel, and the like as is common in the art.

The heavy-ends column 150 may include a distillation column and equipment associated with the distillation column including but not limited to heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 140. Stream 156 may include acetic acid product.

Suitable alternative embodiments for the acetic acid production system 100 may be found in U.S. Pat. No. 6,552,221, which is herein incorporated by reference.

EXAMPLES

To facilitate a better understanding of the disclosure, the following examples of embodiments are given. In no way should the following examples be read to limit, or to define, the scope of the appended claims.

A Vapor Liquid Equilibria (VLE) study (under flash tank conditions) was undertaken in the 3 wt. % to 6 wt. % water range to determine the relative effects of TPPO on HI and $H_2O$ volatility. Additional VLE studies were undertaken with TBPO, which is a slightly more basic version of TPPO. The increased basicity of TBPO leads to a stronger interaction with HI relative to TPPO and suggests that, at least in terms of effect on vapor liquid equilibria, TBPO is a potential replacement for TPPO.

VLE experiments were carried out in glassware. Equipment consisted of a 50 mL flat-bottomed flask, a dean stark tube and a graduated schlenk tube. 20 mLs of solution were used per run. A small aliquot of starting solution was removed from the pot for FTIR analysis before commencement of heating. The pot was lagged with aluminum foil and the schlenk receiving tube placed in a slurried ice bath to minimize evaporation. Using a pre-heated hot plate/stirrer, solutions typically commence distilling within about 10 minutes. Once 2 mLs had been collected in the schlenk receiving tube, the apparatus was removed from the hot plate. An aliquot of the condensed overhead sample from the receiving tube and from the pot were analyzed by FTIR and by UV-vis.

The VLE apparatus operated in adiabatic fashion in which only one equilibrium stage was present and in which there was no enrichment of the vapor in the more volatile component by partial condensation.

Table 2 below shows the projected TPPO concentrations required to maintain distillation column feed HI in the 300-400 ppm range at various reaction water concentrations. The final column in Table 2 contains the projected water concentrations in the distillation column feed (downstream water concentration) associated with corresponding reaction water and TPPO concentrations. These data were projected based on the correlations shown in FIG. 2.

TABLE 2

| Required TPPO Concentration | | | |
| --- | --- | --- | --- |
| Reaction $H_2O$ wt. % | Molarity | Wt. % | Projected DC Feed $H_2O$ wt. % |
| 6 | 0.25 | 6.7 | 9.1 |
| 5 | 0.38 | 10.1 | 8.6 |
| 4 | 0.47 | 12.6 | 7.7 |
| 3 | 0.88 | 23.6 | 6.4 |

While in relative terms, Table 2 shows that the % differential between distillation column (DC) feed and reaction water concentration increases substantially as reaction water concentration is lowered, in absolute terms, DC feed water concentration decreases directionally with decreasing reactor water concentration. It is only the magnitude of this decrease that is muted by increased water volatilization. Therefore, control of the reaction phosphine oxide concentration: water relationship can be used to obtain any target DC feed water concentration.

Figure 3:
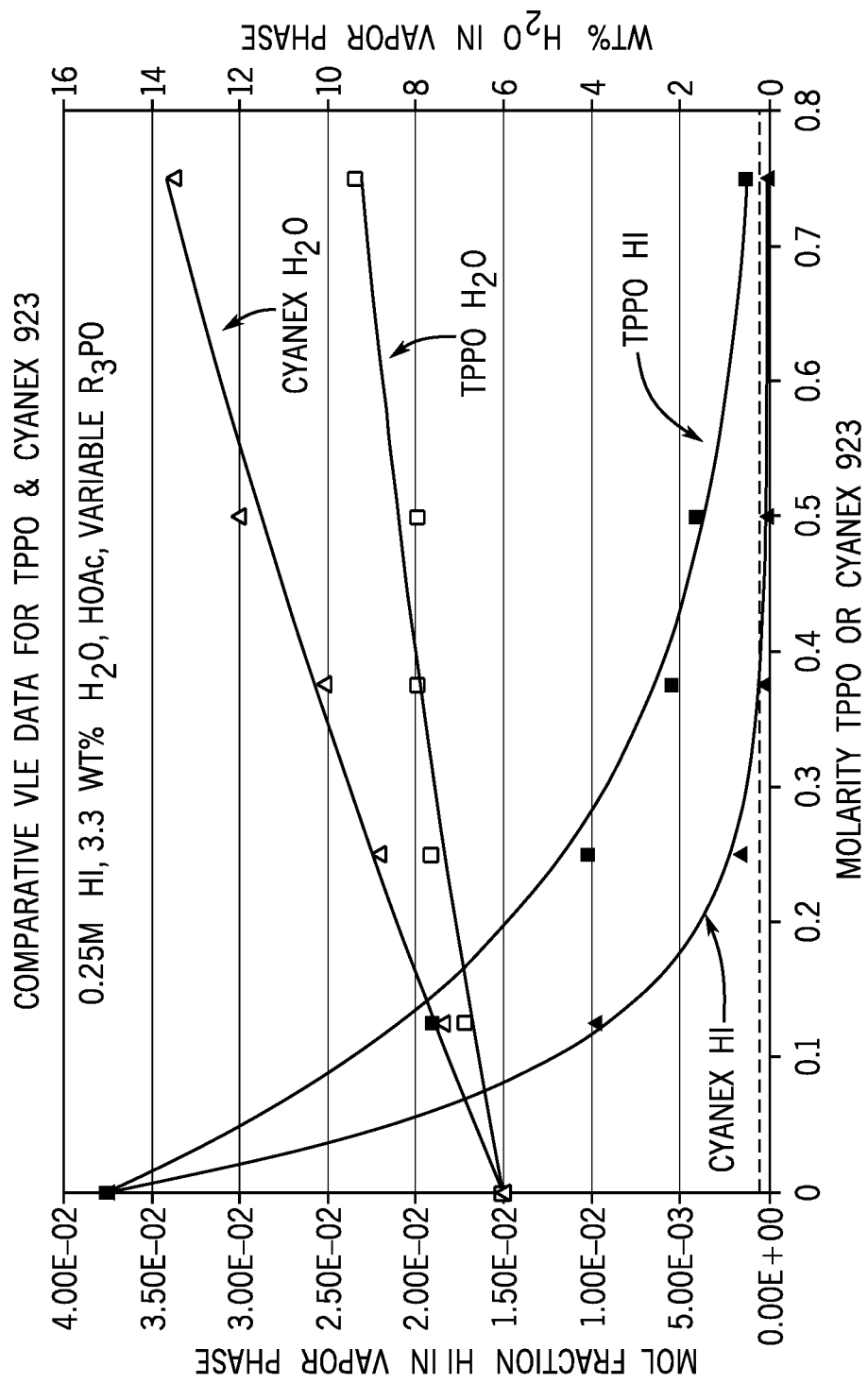
FIG. 3 illustrates Vapor Liquid Equilibria (VLE) data for various process scenarios.
Figure 4:
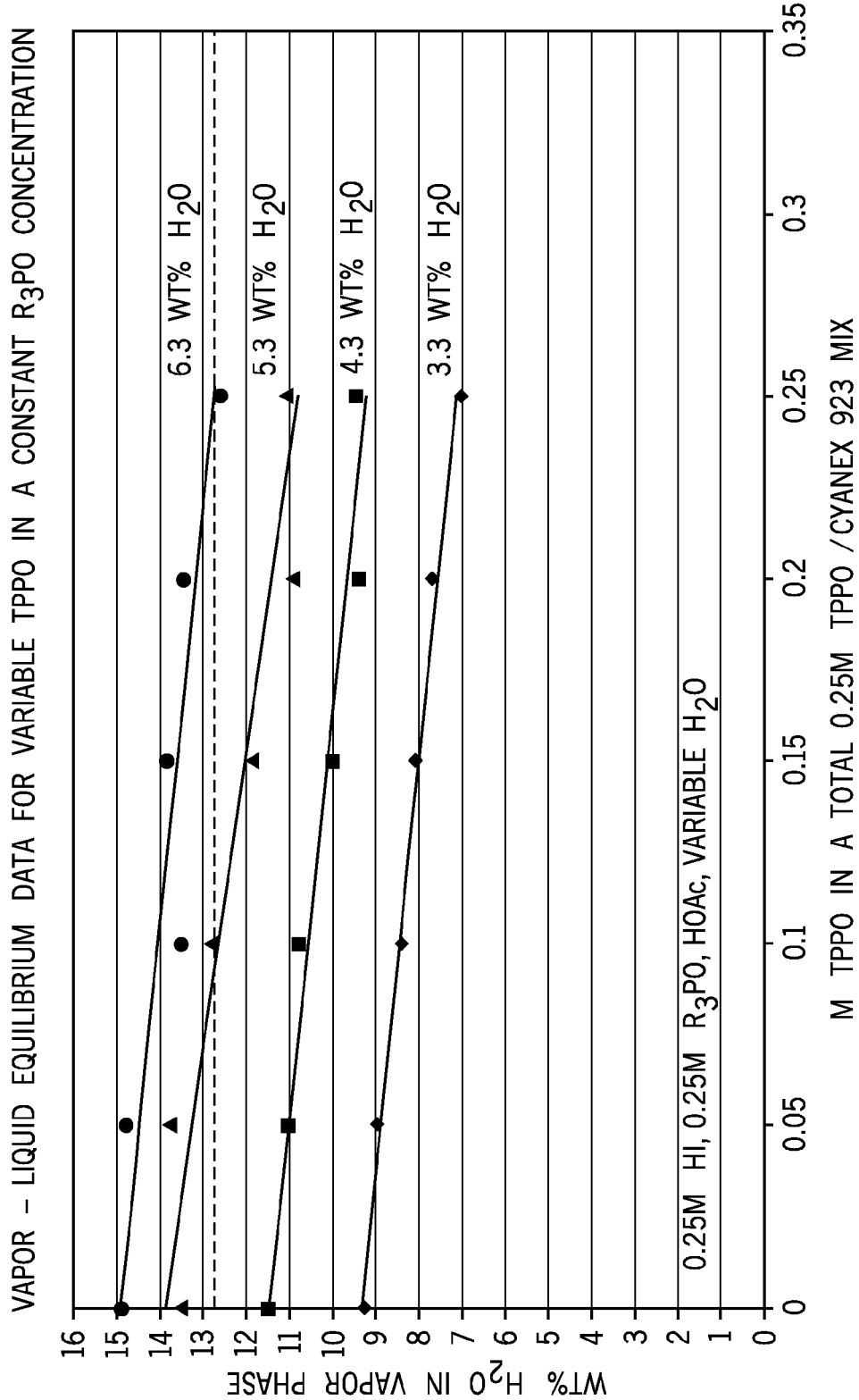
FIG. 4 illustrates Vapor Liquid Equilibria (VLE) data for various process scenarios.

It was further observed that the magnitude of water volatilization is a function of phosphine oxide basicity and FIG. 3 shows increased water volatilization for the more basic Cyanex® 923 relative to TPPO. Thus, the % differential between reactor and DC feed water concentration can be controlled by both phosphine oxide concentration and basicity. FIG. 4 shows that this control can also be obtained by a phosphine oxide mixture, such as utilizing a mixture of phosphine oxides of varying basicity.

CLOSING OF THE DETAILED DESCRIPTION

Therefore, the embodiments as disclosed herein are well adapted to attain the ends and advantages mentioned as well as those that are inherent therein. The particular embodiments disclosed above are illustrative only, as such they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the appended claims. Accordingly, the protection sought herein is as set forth in the claims below.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

What is claimed is:

1. A process for controlling downstream water concentration in an acetic acid production process comprising:
   contacting methanol and carbon monoxide in the presence of a reaction medium under carbonylation conditions sufficient to form a carbonylation product comprising acetic acid, wherein the reaction medium comprises a carbonylation catalyst, water in an upstream water concentration of from 1 wt. % to 14 wt. % water, and a tertiary phosphine oxide;
   recovering acetic acid from the carbonylation product; and
   controlling a downstream water concentration by determining a target water concentration and introducing the tertiary phosphine oxide to the reaction medium at a rate, basicity, concentration or combination thereof sufficient to provide a downstream water concentration within 1 wt. % of the target water concentration.

2. The process of claim 1, wherein the recovering acetic acid comprises:
   flashing the carbonylation product to form a vapor fraction and a liquid fraction;
   separating the vapor stream to form an overhead stream, an acetic acid stream and a bottoms stream; and
   drying the acetic acid stream to remove water therefrom.

3. The process of claim 2, wherein the downstream water concentration is selected from a concentration of water in the carbonylation product, the vapor fraction, the acetic acid stream or combinations thereof.

4. The process of claim 1, wherein the upstream water concentration is from 2 wt. % to 6 wt. %.

5. The process of claim 1, wherein the target water concentration is greater than the upstream water concentration.

6. The process of claim 1, wherein the target water concentration is from 4 wt. % to 15 wt. %.

7. The process of claim 1, wherein a differential between the upstream and target water concentration is at least 1 wt. %.

8. The process of claim 1, wherein a differential between the upstream and target water concentration is less than 10 wt. %.

9. The process of claim 1, wherein a differential between the upstream and target water concentration is from 2 wt. % to 6 wt. %.

10. The process of claim 1, wherein the reaction medium comprises a tertiary phosphine oxide concentration of from 0.2M to 1.0M.

11. The process of claim 1, wherein the downstream water concentration is controlled by increasing basicity of the tertiary phosphine oxide with an increasing target water concentration.

12. The process of claim 1, wherein the downstream water concentration is controlled by increasing a tertiary phosphine oxide concentration with an increasing differential between the upstream and target water concentration.

13. The process of claim 1, wherein the tertiary phosphine oxide comprises a plurality of tertiary phosphine oxides.

14. The process of claim 1, wherein the tertiary phosphine oxide is selected from non-benzoyl containing pentavalent phosphine oxides, compound mixtures of at least four phosphine oxides and pentavalent aryl or alkaryl phosphine oxides comprising one or more benzoyl groups.

15. The process of claim 1, wherein the tertiary phosphine oxide is selected from non-benzoyl containing pentavalent phosphine oxides, compound mixtures of at least four phosphine oxides and combinations thereof.

16. The process of claim 1, wherein the carbonylation conditions comprise a temperature of from 150° C. to 250° C. and a pressure of from 200 psig (1380 kPa) to 2000 psig (13800 kPa).

17. The process of claim 1, wherein the recovery of acetic acid is in the absence of supplemental water addition.

18. An acetic acid production process comprising:
  contacting methanol and carbon monoxide in the presence of a reaction medium under carbonylation conditions sufficient to form a carbonylation product comprising acetic acid, wherein the reaction medium comprises a carbonylation catalyst, water in an upstream water concentration of from 2 wt. % to 6 wt. % water, and a tertiary phosphine oxide;
  flashing the carbonylation product to form a vapor fraction and a liquid fraction;
  separating the vapor stream to form an overhead stream, an acetic acid stream and a bottoms stream;
  drying the acetic acid stream to remove water therefrom; and
  controlling a downstream water concentration by introducing the tertiary phosphine oxide to the reaction medium at a rate, basicity, concentration or combination thereof sufficient to provide a downstream water concentration that is greater than the upstream water concentration and is from 4 wt. % to 15 wt. %, wherein the downstream water concentration is selected from a concentration of water in the carbonylation product, the vapor fraction, the acetic acid stream or combinations thereof.

19. The process of claim 18, wherein a differential between the upstream and target water concentration is from 2 wt. % to 10 wt. %.

20. The process of claim 18, wherein the tertiary phosphine oxide is selected from non-benzoyl containing pentavalent phosphine oxides, compound mixtures of at least four phosphine oxides and pentavalent aryl or alkaryl phosphine oxides comprising one or more benzoyl groups.

* * * * *

UNITED STATES PATENT AND TRADEMARK OFFICE
CERTIFICATE OF CORRECTION

PATENT NO. : 9,428,434 B2
APPLICATION NO. : 14/964793
DATED : August 30, 2016
INVENTOR(S) : Noel C. Hallinan et al.

Page 1 of 1

It is certified that error appears in the above-identified patent and that said Letters Patent is hereby corrected as shown below:

In the Specification

Column 1    Line 45    Delete "east" and insert --least--
Column 12   Line 62    Delete "H2O" and insert --$H_2O$--

Signed and Sealed this
First Day of January, 2019

Andrei Iancu
*Director of the United States Patent and Trademark Office*